US008314271B2

(12) United States Patent
Jacoby

(10) Patent No.: US 8,314,271 B2
(45) Date of Patent: Nov. 20, 2012

(54) SELECTIVE PREPARATION OF SOME 2-ALKOXY-ETHANOL DERIVATIVES

(75) Inventor: Denis Jacoby, Nyon (CH)

(73) Assignee: Firmenich SA, Geneva (CH)

( * ) Notice: Subject to any disclaimer, the term of this patent is extended or adjusted under 35 U.S.C. 154(b) by 469 days.

(21) Appl. No.: 12/677,235

(22) PCT Filed: Sep. 8, 2008

(86) PCT No.: PCT/IB2008/053617
§ 371 (c)(1),
(2), (4) Date: Mar. 9, 2010

(87) PCT Pub. No.: WO2009/034510
PCT Pub. Date: Mar. 19, 2009

(65) Prior Publication Data
US 2010/0197973 A1    Aug. 5, 2010

(30) Foreign Application Priority Data
Sep. 11, 2007   (WO) .................. PCT/IB2007/053656

(51) Int. Cl.
*C07C 41/08*       (2006.01)
*C07C 43/13*       (2006.01)
*C08J 11/16*       (2006.01)

(52) U.S. Cl. ......... 568/670; 568/662; 568/675; 568/678

(58) Field of Classification Search .................. None
See application file for complete search history.

(56) References Cited

U.S. PATENT DOCUMENTS

| 5,162,446 A | 11/1992 | Gibler et al. ................. 525/338 |
| 5,717,111 A | 2/1998 | Koehler et al. ............... 549/266 |
| 5,770,678 A | 6/1998 | Drysdale et al. ............. 528/233 |

FOREIGN PATENT DOCUMENTS

| EP | 0 739 889 B1 | 10/1996 |
| FR | 2 447 363 A1 | 8/1980 |

OTHER PUBLICATIONS

International Search Report and Written Opinion of the International Searching Authority, application No. PCT/IB2008/053617, Apr. 22, 2009.

*Primary Examiner* — Rosalynd Keys
(74) *Attorney, Agent, or Firm* — Winston & Strawn LLP

(57) ABSTRACT

A method for producing certain 2-alkoxy-ethanol derivatives by depolymerising oligomeric or polymeric polyglycol derivatives in the presence of alcoholate or 1,3-diketonate derivatives of zirconium, titanium, aluminum or molybdenum.

9 Claims, No Drawings

SELECTIVE PREPARATION OF SOME 2-ALKOXY-ETHANOL DERIVATIVES

This application is a 371 filing of International Patent Application PCT/IB2008/053617, filed Sep. 8, 2008.

TECHNICAL FIELD

The present invention relates to the field of organic chemistry and more specifically to a method for producing some 2-alkoxy-ethanol derivatives. The present method comprises the steps of depolymerising some oligomeric or polymeric polyglycol derivatives in the presence of alcoholate 1,3-diketonate derivatives of zirconium, titanium, aluminium or molybdenum.

PRIOR ART

The simplest way to produce 2-alkoxy-ethanol derivatives comprises the addition of an alcohol to an epoxide to obtain a 1/1 adduct (i.e. the desired product). However this method gives, in the vast majority of cases, a number of oligomeric or polymeric by-products (i.e. 2-alkoxy-polyethyleneglycol derivatives). These by-products are undesirable and are a lost of precious starting alcohol. Furthermore, said method implies working conditions necessitating low conversations in order to minimize the formation of said by-products and the lost of the starting alcohol.

In order to recycle the undesired by products mentioned above, in the prior art there are reported a number of methods (e.g. treatment by strong protic acids) which allow only the conversion of a 2-alkoxy-polyethyleneglycol derivative directly to the free starting alcohol (for instance see U.S. Pat. No. 5,770,678). This solution is not satisfactory for obvious reasons.

To the best of our knowledge, in the prior art there is only one document suggesting that a selective conversion (i.e. that stops exactly at the desired product: the 1/1 adduct) of a 2-alkoxy-polyethyleneglycol derivative can be performed (FR 2447363). However this document discloses hydrogenation conditions requiring very strong temperatures (e.g. 250° C.) where a very limited number of substrates can survive.

Therefore there is still a need for a process allowing carrying out the invention's process under milder conditions.

DESCRIPTION OF THE INVENTION

We have discovered that some 2-alkoxy-ethanols can be selectively produced by treating a polyethylene glycol derivative with a particular type of zirconium complex.

Therefore, an aspect of the present invention concerns a process for producing a compound of formula

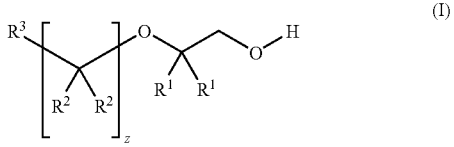

wherein z represents 1 or 0, and
each $R^1$, independently from each other, represents a hydrogen atom or a methyl or ethyl group, or the two $R^1$ taken together represent a $(CH_2)_m$ group, m representing 3, 4, or 5;
each $R^2$, independently from each other, represents a hydrogen atom or a methyl or ethyl group, or the two $R^2$ taken together represent a $(CH_2)_m$ group, m representing 3, 4, or 5; and
$R^3$ represents a phenyl group optionally substituted, a saturated or unsaturated $C_5$-$C_6$ cyclic hydrocarbon moiety optionally substituted, or a $CH(R^4)_2$ or $R^4CH=CR^4$ moiety, $R^4$ representing a $C_1$-$C_6$ alkyl or alkenyl group optionally substituted;
said process comprising the step of reacting the corresponding compound of formula

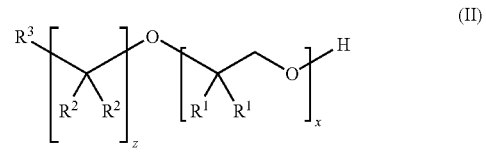

wherein z, $R^1$, $R^2$ and $R^3$ are defined as in formula (I) and x represents an integer comprised between 2 and 10;
with at least one metal compound of formula $M(R^5)_{(n-2y)}(R^6)_y$, wherein y is 0, 1 or 2;
M representing Zr or Ti, and n is 4, or Al and n is 3, or $Mo(O_2)_2$ and n is 2;
$R^5$ representing, independently from each other, a $C_1$-$C_6$ alkoxylate group or a $C_5$-$C_8$ 1,3-diketonate, and
$R^6$ representing a 1,2- or 1,3-dialkoxylate or a 1,2-diphenoxylate.

According to a particular embodiment of the invention, the compounds of formula (I) are those wherein z represents 1, each $R^1$, independently from each other, represents a hydrogen atom or a methyl group, or the two $R^1$ taken together represent a $(CH_2)_m$ group, m representing 3 or 4;
each $R^2$, independently from each other, represents a hydrogen atom or a methyl group, or the two $R^2$ taken together represent a $(CH_2)_m$ group, m representing 3 or 4; and
$R^3$ represents a saturated or unsaturated $C_5$-$C_6$ cyclic hydrocarbon moiety optionally substituted, or a $CH(R^4)_2$ or $R^4CH=CR^4$ moiety, $R^4$ representing a $C_1$-$C_4$ alkyl group optionally substituted.

According to an embodiment of the invention, the corresponding compound of formula (II) can be one wherein x represents an integer comprised between 2 and 5.

In all the embodiments of the invention, optional substituents of $R^3$ are one, two or three $C_1$-$C_3$ alkyl, alkenyl or alkoxy groups, for example methyl or ethyl.

As non-limiting typical examples of $R^3$ groups one may cite the following: 3,3-dimethyl-cyclohexyl, 3,3-dimethyl-cyclohex-1-en-1-yl, 4-methyl-pent-2-en-2-yl, 5-methyl-cyclohex-3-en-1-yl, 2-methyl-cyclohexyl.

According to a particular embodiment, one or two $R^1$, per glycol unit of compound (I) or (II), are a methyl group. Similarly, at least one $R^2$ is a methyl group.

The starting compound (II) can be simply prepared by adding an alcohol of formula $R^3(R^2)_2COH$ to an excess of the epoxide $(C(R^1)_2CH_2))O$ under conditions well known by a person skilled in the art.

The invention's process allows the preparation of the desired 2-alkoxy-ethanol without being impeded by the need of low conversions conditions to avoid the formation of polymeric products, and therefore the overall yield and global productivity is improved.

As previously mentioned, the use of a metal compound as described above allows a selective conversion of the polyglycolic chain of (II) into the corresponding compound (I), which is the equivalent of a selective 1/1 addition on an alcohol to an epoxide, i.e. the alcohol $R^3(R^2)_2COH$ is not the main product.

In particular the metal compound can be one of formula $M(R^5)_{(n-2y)}(R^6)_y$, wherein y is 0 or 1; M representing Zr or Ti, and n is 4, or Al and n is 3; $R^5$ representing, independently from each other, a $C_1$-$C_6$ alkoxylate group or a $C_5$-$C_8$ 1,3-diketonate; and $R^6$ representing a 1,2- or 1,3-dialkoxylate.

According to a particular embodiment of the invention, said metal compound can be a compound of formula $M(R^5)_4$, M being Zr or Ti, or of formula $Al(R^5)_3$, $R^5$ having the meaning described above.

According to a particular embodiment of the invention, said metal compound can be one of formula $Zr(R^5)_4$ or $Al(R^5)_3$, $R^5$ having the meaning described above.

According to any one of the above embodiments, all $R^5$ groups represent an alkoxylate group or a 1,3-diketonate group.

According to any one of the above embodiments, the $R^5$ group is $^-$OMe, $^-$OEt, $^-$OPr, $^-$O$^i$Pr, $^-$BuO, $^t$BuO or acetylacetonate, in particular OPr, $^-$O$^i$Pr, BuO, $^t$BuO or acetylacetonate.

According to a particular embodiment of the invention, the $R^6$ group is $^-$OCH$_2$CH$_2$O$^-$.

The metal compounds are known compounds and the methods for their preparation is well known in the literature.

Useful quantities of metal compound, added to the reaction mixture, may be comprised in a relatively large range. One can cite, as non-limiting examples, ranges between 0.005 and 1 molar equivalents, relative to the compound of formula (II), preferably between 0.01 and 0.2 molar equivalents.

The depolymerization reaction can be carried out in the absence of a solvent. However, it can be also carried out in the presence of a solvent, and in this case such a solvent could be a saturated or aromatic hydrocarbon having a boiling point above 250° C., e.g. the ones known also under the ESSO's tradenames Marcol® or Primol® or the Hüs's tradename Marlotherm®.

The temperature at which the invention's depolymerization can be carried out is comprised between 80° C. and 220° C., more preferably in the range of between 120° C. and 190° C. Of course, a person skilled in the art is also able to select the preferred temperature as a function of the melting and boiling point of the starting and/or final products as well as the desired time of reaction or conversion.

In some cases, it can be convenient to carry out the invention's process under reduced pressures conditions, such as under pressures comprised between 0.1 and 1000 mbar, preferably between 0.5 and 100 mbar.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. All substrates and solvents were distilled from appropriate drying agents under Ar. NMR spectra were recorded on a Bruker AM-400 ($^1$H at 400.1 MHz) spectrometer and normally measured at 300 K, in CDCl$_3$ unless indicated otherwise. Chemical shifts are listed in ppm.

Example 1

Preparation of the Oligomeric Product

The oligomeric compound (II) can be prepared according to any standard methods well known by a person skilled in the art. E.g., 1-(3',3'-Dimethyl-1'-cyclohexyl)-1-ethanol was reacted with isobutylene oxide in the presence of BF$_3$ as catalyst, under condition of excess of the starting alcohol. The reaction leads to a mixture of products of mono- and di-addition of the epoxide according to the following scheme:

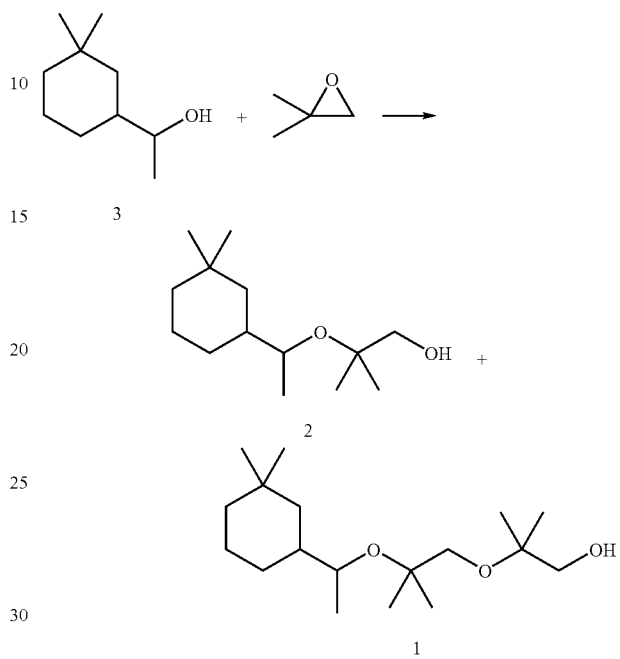

The oligomeric product 1 is easily recovered from the residual material of the fractional distillation of the compound 2 and purified by flash distillation.

Depolymerization of the Oligomeric Product 1:

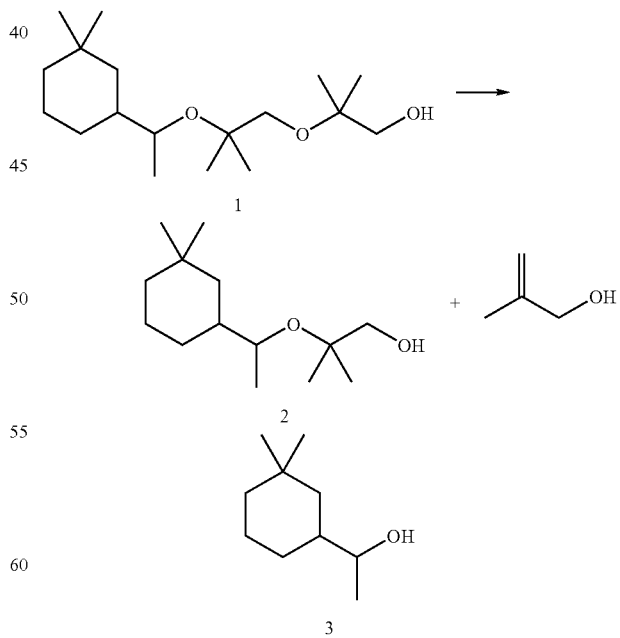

A 250 ml laboratory reactor equipped with a short packed column, a reflux condenser and a −80° C. cooled trap, was charged with 100 g of the oligomeric product 1 (72% purity)

in the presence of 4 g of zirconium tetrapropoxide (70% in propanol). The mixture is progressively heated to 150° C. under vacuum (20 mbar). The pressure is progressively reduced to 10 mbar and the reactor temperature is allowed to increase to 170° C. and then the reaction is left running for 16 hours. During this time, the monomeric compound 2 is distilled into a flask while the volatile compounds (mainly propanol and methallyl alcohol) are collected in the cooled trap.

The distillate thus obtained contains mainly: alcohol 2: 76%; starting alcohol 3: 2.7%; oligomeric compound 1: 11%.

The fractional distillation of the above distillate affords 42 g of the pure alcohol 2 (diastereoisomeric mixture) corresponding to 55% mol yield.

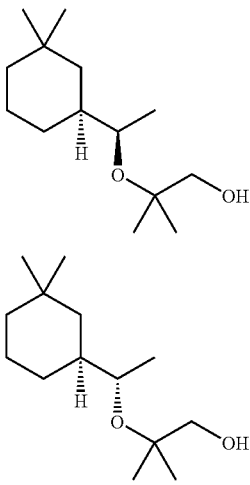

¹H-NMR: 0.86 (s, 3H); 0.90 (s, 3H); 1.05 (d, 3H); 1.13 (s, 3H); 1.15 (s, 3H); 0.7-1.9 (m, 9H); 3.30 (s, 2H); 3.35 (m, 1H)

GC-MS 2a: 228 (M⁺., 0); 197 (10); 139 (96); 123 (18); 117 (27); 97 (25); 83 (96); 73 (100); 69 (35); 55 (42); 41 (25)

GC-MS 2b: 228 (M⁺., 0); 197 (10); 139 (99); 123 (18); 117 (31); 97 (24); 83 (100); 73 (99); 69 (35); 55 (50); 41 (29)

Example 2

Depolymerization of the Oligomeric Product 1 with Various Catalysts (General Procedure)

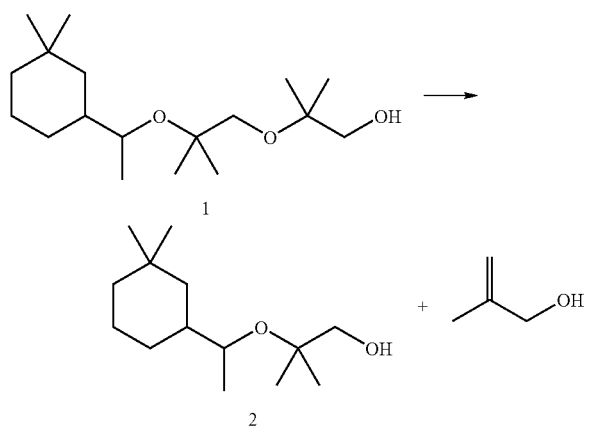

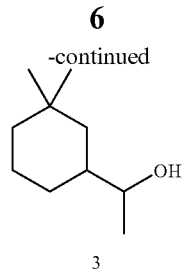

A 250 ml laboratory reactor equipped with a short packed column, a reflux condenser and a −80° C. cooled trap, was charged with 100 g of the oligomeric product 1 (prepared according to the above procedure, 72% purity) in the presence of the catalyst. The mixture is progressively heated to 150° C. under vacuum (20 mbar). The pressure is progressively reduced to 10 mbar and the reactor temperature is allowed to increase to 165° C. and then the reaction is left running for 4-5 h hours. During this time, the monomeric compound 2 is distilled into a flask while the volatile compounds (mainly propanol and methallyl to alcohol) are collected in the cooled trap.

The distillate thus obtained is fractionated and the alcohol 2 is isolated as the pure product. The following table outlines the tested catalysts and the corresponding results.

| Catalyst | Mol equivalent | Distillate weight | Alcohol 2 % | Mol yield % |
|---|---|---|---|---|
| Zr(OPr)₄ (Example 1) | 0.035 | 44.6 g | 69% | 56 |
| Ti(OⁱPr)₄ | 0.035 | 25.4 g | 60% | 27.8% |
| Zr(acac)₄ | 0.035 | 22.8 g | 45% | 18.7% |
| Al(OᵗBu)₃ | 0.035 | 51 g | 63% | 58.7% |
| Al(OˢᵉᶜBu)₃ | 0.035 | 33.6 g | 33% | 20.3% |
| Al(OⁱPr)₃ | 0.035 | 32.4 g | 38% | 22.5% |

What is claimed is:

1. A process for producing a compound of formula (I):

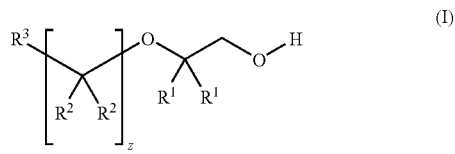

wherein
z represents 1 or 0, and
each $R^1$, independently from each other, represents a hydrogen atom or a methyl or ethyl group, or the two $R^1$ taken together represent a $(CH_2)_m$ group, m representing 3, 4, or 5;
each $R^2$, independently from each other, represents a hydrogen atom or a methyl or ethyl group, or the two $R^2$ taken together represent a $(CH_2)_m$ group, m representing 3, 4, or 5; and
$R^3$ represents a phenyl group optionally substituted, a saturated or unsaturated $C_5$-$C_6$ cyclic hydrocarbon moiety optionally substituted, or a $CH(R^4)_2$ or $R^4CH=CR^4$ moiety, $R^4$ representing a $C_1$-$C_6$ alkyl or alkenyl group optionally substituted; and the substituents of said $R^3$ group are one, two or three $C_1$-$C_3$ alkyl, alkenyl or alkoxy groups;

wherein the process comprises reacting the corresponding compound of formula (II):

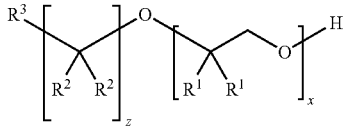

(II)

wherein z, $R^1$, $R^2$ and $R^3$ are defined as in formula (I) and x represents an integer comprised between 2 and 10;
with at least one metal compound of formula $M(R^5)_{(n-2y)}(R^6)_y$, wherein y is 0, 1 or 2;
wherein:
  M represents Zr or Ti, and n is 4, or Al and n is 3, or $Mo(O_2)_2$ and n is 2;
  $R^5$ represents, independently from each other, a $C_1$-$C_6$ alkoxylate group or a $C_5$-$C_8$ 1,3-diketonate, and
  $R^6$ represents a 1,2- or 1,3-dialkoxylate or a 1,2-diphenoxylate.

2. The process according to claim 1, wherein the compounds of formula (I) are those wherein:
  z represents 1,
  each $R^1$, independently from each other, represents a hydrogen atom or a methyl group, or the two $R^1$ taken together represent a $(CH_2)_m$ group, m representing 3 or 4;
  each $R^2$, independently from each other, represents a hydrogen atom or a methyl group, or the two $R^2$ taken together represent a $(CH_2)_m$ group, m representing 3 or 4; and
  $R^3$ represents a saturated or unsaturated $C_5$-$C_6$ cyclic hydrocarbon moiety optionally substituted, or a $CH(R^4)_2$ or $R^4CH=CR^4$ moiety, $R^4$ representing a $C_1$-$C_4$ alkyl group optionally substituted.

3. The process according to claim 1, wherein the compounds of formula (I) are those wherein:
  $R^3$ is 3,3-dimethyl-cyclohexyl, 3,3-dimethyl-cyclohex-1-en-1-yl, 4-methyl-pent-2-en-2-yl, 5-methyl-cyclohex-3-en-1-yl or 2-methyl-cyclohexyl;
  one or two $R^1$, per glycol unit of compound (I) or (II), are a methyl group; and
  at least one $R^2$ is a methyl group.

4. The process according to claim 1, wherein the metal is a compound of formula $M(R^5)_{(n-2y)}(R^6)_y$, wherein y is 0 or 1 and:
  M represents Zr or Ti, and n is 4, or
  M represents Al and n is 3;
  with $R^5$ representing, independently from each other, a $C_1$-$C_6$ alkoxylate group or a $C_5$-$C_8$ 1,3-diketonate; and $R^6$ representing a 1,2- or 1,3-dialkoxylate.

5. The process according to claim 4, wherein the metal compound is of formula $Ti(R^5)_4$.

6. The process according to claim 4, wherein the metal compound is of formula $Zr(R^5)_4$.

7. The process according to claim 4, wherein the metal compound is of formula $Al(R^5)_3$.

8. The process according to claim 4, wherein all $R^5$ groups represent an alkoxylate group or a 1,3-diketonate group.

9. The process according to claim 4, wherein the metal compound is added to the reaction mixture in quantities ranging between 0.005 and 1 molar equivalents, relative to the compound of formula (II).

* * * * *